US012295983B2

(12) United States Patent
Feistel et al.

(10) Patent No.: US 12,295,983 B2
(45) Date of Patent: May 13, 2025

(54) **USE OF EXTRACTS OF THE LEAVES OF LEMON VERBENA (*ALOYSIA CITRIODORA*) FOR INCREASING THE NEURONAL, CEREBRAL AVAILABILITY OF NEUROTRANSMITTERS SELECTED FROM THE GROUP OF SEROTONIN, DOPAMINE, NORADRENALINE**

(71) Applicant: Finzelberg GMBH & Co. KG, Andernach (DE)

(72) Inventors: Björn Feistel, Andernach (DE); Bernd Walbroel, Königswinter (DE); Bernd L. Fiebich, Freiburg (DE); Kurt Appel, Bramsche (DE)

(73) Assignee: Finzelberg GMBH & Co. KG, Adernach (DE)

( * ) Notice: Subject to any disclaimer, the term of this patent is extended or adjusted under 35 U.S.C. 154(b) by 876 days.

(21) Appl. No.: 17/293,518

(22) PCT Filed: Nov. 14, 2019

(86) PCT No.: PCT/EP2019/081392
§ 371 (c)(1),
(2) Date: May 13, 2021

(87) PCT Pub. No.: WO2020/099595
PCT Pub. Date: May 22, 2020

(65) Prior Publication Data
US 2022/0031794 A1 Feb. 3, 2022

(30) Foreign Application Priority Data
Nov. 14, 2018 (EP) .................................... 18206340

(51) Int. Cl.
*A61K 36/85* (2006.01)
*A61P 25/00* (2006.01)

(52) U.S. Cl.
CPC .............. *A61K 36/85* (2013.01); *A61P 25/00* (2018.01); *A61K 2236/30* (2013.01)

(58) Field of Classification Search
None
See application file for complete search history.

(56) References Cited

U.S. PATENT DOCUMENTS

| | | |
|---|---|---|
| 2006/0280820 A1 | 12/2006 | Balan et al. |
| 2014/0248652 A1* | 9/2014 | Thiruvengadam ........................ G01N 33/5008 702/19 |

FOREIGN PATENT DOCUMENTS

| | | |
|---|---|---|
| CN | 102309622 B | 2/2014 |
| CN | 10739711 A | 11/2017 |
| DE | 10359384 A1 | 7/2005 |
| DE | 10-2007-052223 A1 | 5/2009 |
| DE | 10-2011-078432 A1 | 1/2013 |
| JP | 2002-233330 A | 8/2002 |
| JP | 2004-059463 A | 2/2004 |
| JP | 2004-250445 A | 9/2004 |
| JP | 2005-126366 A | 5/2005 |
| JP | 2007-514705 A | 6/2007 |
| JP | 2010-202606 A | 9/2010 |
| KR | 10-2013-0089384 A | 8/2013 |
| KR | 2017-0001583 A | 1/2017 |
| WO | 2005-058338 A1 | 6/2005 |
| WO | 2010-052680 A2 | 5/2010 |

OTHER PUBLICATIONS https://www.webmd.com/add-adhd/childhood-adhd/preventing-adhd—accessed Feb. 13, 2024.*
"Vacuum Drying"; https://www.comsol.com/model/vacuum-drying-42561—accessed Sep. 24, 2024.*
Funes (Food Chemistry (2009), vol. 117, pp. 589-598).*
Tsolaki (International Journal of Alzheimer's Disease (2014), vol. 2014, article ID No. 349249, 10 pages).*
Jiménez-Ferrer et al., "Anxiolytic effect of fatty acids and terpenes fraction from Aloysia triphylla: Serotoninergic, GABAergic and glutamatergic implications", Biomedicine & Pharmacotherapy, vol. 96, p. 320-327, (2017).
Office Action from corresponding Chinese Patent Application No. 2019800755642 dated Jan. 27, 2022.
Carpinella et al., "Screening for Acetylcholinesterase Inhibitory Activity in Plant Extracts from Argentina", Phytotherapy Research, p. 259-263, (Feb. 2010).
Planox L, "Standardized Herbal Extract from the Lemon verbena as a Health Ingredient for Functional Food", Anoxymer, (Dec. 15, 2003).
Ragone et al., "Sedative and Cardiovascular Effects of Aloysia citriodora Palau, on Mice and Rats", Latin American Journal of Pharmacy, p. 79-86, (Jan. 1, 2010).
Veisi et al., "Assessment of Aqueous Extract of Lemon verbena on Anxiety-like Behavior in Rats", Journal of Pharmaceutical Negative Results, vol. 6 Issue 1, p. 37-39, (Jan. 1, 2015).
Wannamacher et al., "Plants Employed in the Treatment of Anxiety and Insomnia II, Effect of Infusions of Aloysia-Triphylla on Experimental Anxiety in Normal Volunteers", Clarivate Analytics, Database Online, (1990).
Xu et al., "Effect of Different Component Ratio of Astragalus Total Saponins and Verbena Total Glycosides on the Cerebal Infraction Area and Serum Biochemical Indicators in the Focal Cerebral Ischemia-Reperfusion Rat Model", Saudi Pharmaceutical Journal, p. 660-665, (May 2017).

(Continued)

*Primary Examiner* — Susan Hoffman
(74) *Attorney, Agent, or Firm* — Christensen, Fonder, Dardi PLLC; Diane E. Bennett; Peter S. Dardi

(57) ABSTRACT

The aim of the invention is to provide preparations and extracts of lemon verbena (*Aloysia citriodora*, or its synonyms) for the prophylaxis of mental stress, for increasing cognitive performance and for treating ADHS. For this purpose, preparations and extracts of lemon verbena (*Aloysia citriodora*, or its synonyms) are used, particularly in the form of hydroalcoholic extracts. These extracts can be used in food products, food supplements, supplementary balanced diets or pharmaceutical preparations.

16 Claims, 7 Drawing Sheets

(56) References Cited

OTHER PUBLICATIONS

International Search Report for corresponding Patent Application No. PCT/EP2019/081392 dated Jan. 24, 2020.
Razavi et al., "Anti-anxiety and hypnotic effects of ethanolic and aqueous extracts of Lippia citriodora leaves and verbascoside in mice", Avicenna Journal of Phytomed, vol. 7 No. 4, p. 353-365, (2017).
Shiao et al., "Acteoside and Isoacteoside Protect Amyloid β Peptide Induced Cytotoxicity, Cognitive Deficit and Neurochemical Disturbances In Vitro and In Vivo", International Journal of Molecular Sciences, vol. 18 No. 895, p. 1-16, (Apr. 2017).
Zhu et al., "Central Anti-Fatigue Activity of Verbasoside", Neuroscience Letters vol. 11 No. 616, p. 75-79, (Jan. 2016).
Office Action from corresponding Japanese Patent Application No. 2021-526672 dated Jul. 4, 2023.
Office Action from corresponding Japanese Patent Application No. 2021-526672 dated Mar. 12, 2024.
Office Action from corresponding European Patent Application No. 19813247.4 dated Feb. 27, 2024.
Buchwald-Werner et al., "Effects of lemon verbena extract (Recoverben®) supplementation on muscle strength and recovery after exhaustive exercise: a randomized, placebo-controlled trial", Journal of the International Society of Sports Nutrition, vol. 15(5), p. 1-10, (2018).
Choupani et al., "Antioxidant Properties of Various Solvent Extracts of Lemon Verbena (*Lippia citriodora*) Leaves", International journal of Advanced Biological and Biomedical Research, vol. 2 Issue 4(2), p. 494-500, (2014).
Hamedi et al., "A Survey on Chemical Constituents and Indications of Aromatic Waters Soft Drinks (Hydrosols) Used in Persian Nutrition Culture and Folk Medicine for Neurological Disorders and Mental Health", Journal of Evidence-Based Complementary & Alternative Medicine, vol. 22(4), p. 744-752, (2017).
Rafiee et al., "Effect of lemon verbena powder and vitamin C on performance and immunity of heat-stressed broilers", Journal of Animal Physiology and Animal Nutrition, 100(5), 807-812, (Feb. 2016).
Office Action from corresponding Indian Patent Application No. 202117021272 dated Oct. 4, 2023.

\* cited by examiner

• transgenic animals with ß-amyloid expression that were treated only with water (control group, vehicle)
◇ non-transgenic animals (healthy) that were treated only with water
△ lemon verbena extract according to the invention (extractant 50% v/v EtOH), Lot UB2010-91
▩ lemon verbena extract according to the invention (extractant 30% v/v EtOH), Lot UB2010-97

USE OF EXTRACTS OF THE LEAVES OF LEMON VERBENA (*ALOYSIA CITRIODORA*) FOR INCREASING THE NEURONAL, CEREBRAL AVAILABILITY OF NEUROTRANSMITTERS SELECTED FROM THE GROUP OF SEROTONIN, DOPAMINE, NORADRENALINE

CROSS REFERENCE TO RELATED APPLICATIONS

This application is a National Stage filing of PCT Application No. PCT/EP2019/081392 filed Nov. 14, 2019, entitled "Use Of Extracts Of The Leaves Of Lemon Verbena (*Aloysia citriodora*) For Increasing The Neuronal, Cerebral Availability Of Neurotransmitters Selected From The Group Of Serotonin, Dopamine, Noradrenaline", which claims priority to European Patent Application No. 18206340.4, filed Nov. 14, 2018, both which are incorporated herein by reference.

Botanically, the lemon verbena (plant species: *Aloysia citriodora* PALÁU) belongs to the genus beebrushes (*Aloysia*) in the verbena family (Verbenaceae).

Various synonymous terms exist in the literature for lemon verbena: *Aloysia triphylla* (L'Hérit.) Kuntze/*Lippia citriodora* Kunth/*Verbena triphylla* L'Herit., which can also be found in the European Pharmacopoeia monograph (Ph. Eur. Chapter 1834).

The scientific name *Aloysia citriodora* (formerly *Lippia citriodora*) refers to the specific scent and taste of the leaves like citrus flavors by the reference "*citriodora*". The synonymous name of *Aloysia triphylla* (formerly *Verbena triphylla*) refers to the arrangements of the leaves on the branches by the reference "*triphylla*"=three leaves.

Correct international designations of the lemon verbena are:
German: Zitronenverbene, Zitronenstrauch
Austrian: Luiserkraut
English: lemon verbena, lemon-scented verbena
French: verveine citronelle, verveine odorante
Dutch: Citroenverbena, Citroenstruik
Portuguese: limonette, buona Luisa
Spanish: cedron, hierba Luisa In colloquial German, names like "Zitronenkraut" (lemon herb) "Verbenenkraut" (verbena herb) are often used incorrectly in parallel. In some publications that are predominantly in French, all genera of the Verbenaceae are occasionally subsumed under the name of "vervein" but are also used as a synonym of *Verbena* spp., i.e., the iron herbs, but sometimes also for the lemon verbena. Thus, a clear assignment of the term "verveine" to the species *Aloysia citriodora* or to *Verbena officinalis* is not always unambiguously derivable, and always needs to be clarified from the context in each individual case.

Within the family Verbenaceae, the genus of the beebrushes (*Aloysia*) is different from both the sweet herbs (*Lippia*) with, for example, the representatives "Aztec sweet herb" (*Lippia dulcis* TREV.) or "Mexican oregano" (*Lippia graveolens* H. B. & K.), and the about 250 verbenas (*Verbena*), to which the traditional medicinal plant "common vervain" (*Verbena officinalis* L.) belongs.

Botanically, the most striking characteristic is the fact that plants of the genus *Aloysia* grow as perennial deciduous shrubs that are up to 6 meters high, whereas the verbenas mostly grow as annual herbs and reach a height of only about 70 cm, while the Aztec sweet herb grows flat and remains close to the soil, reaching a height of up to about 20 cm.

The lemon verbena is a plant originating in South America, which can be found growing wild mainly in the regions of Chile and Uruguay. In Europe, because of its lack of frost tolerance, the lemon verbena is cultivated only in the Southern parts, mainly in France and Spain. The leaves of the lemon verbena are usually light green, with a slightly serrate (saw-toothed) edge, lanceolate or acute, and glabrous. The length of the leaves (lamina) varies from 3 to 10 cm, while the width of the leaves may be from 0.5 to 3 cm. On the leaves, there are usually small dots (so-called oil glands), which contain the characteristic essential oil and unfold the lemon-like scent when touched.

From *Aloysia citriodora*, the leaves are usually used, whereas from common vervain of Aztec sweet herb, the entire aerial plant parts (stems, shoot tips, leaves, and flowers) are used. Since there is repeatedly confusion in the current language, two separate monographs have appeared in the European Pharmacopoeia, which allow for differentiation, referring to the leaves of the lemon verbena (Ph. Eur. 1834, monograph lemon verbena leaf) or to the herb of the common vervain (Ph. Eur. 1854, monograph *Verbena officinalis* herba). Also, the analytical lead compound from the leaves of the lemon verbena according to Ph. Eur. 1834, described as an acteoside, is found in the literature under the synonymous name of verbascoside, which often makes a clear assignment more difficult.

DE 10 2011 078 432 A1 describes the use of essential oils and their components from a wide variety of plants in the treatment of hyperkinetic disorders. Inter alia, the description correctly translates common vervain with "*Verbena officinalis*" in paragraph [0014], but in paragraphs [0036], [0046] and [0049], common vervain is incorrectly equated to *Lippia citriodora* Kunze. In the Examples, a botanical designation is no longer used, but the claims change back to *Verbena officinalis*. This shows in an exemplary way how imprecisely the terms are handled. Traditionally, the fresh or dried leaves of lemon verbena are employed as a flavor additive or medicinal plant. The therapeutic applications described include the following properties: antioxidative, galactogogue, analgesic, antibacterial, antipyretic, muscle relaxant, and diuretic. The components of the essential oils and the group of flavonoids are said to be co-responsible for the very broad range of active substances. Consistently, the Ph. Eur. monograph prescribes a minimum content of 3 ml/kg of essential oil and 2.5% acteoside and a DC fingerprint for the presence of flavonoids for lemon verbena leaves (lemon verbena folium) in the quality specification for dried whole leaves.

Although the essential oil is very often quoted as a group of active components, characteristic chromatographic analyses for the specific components of the oil are not precisely described in combination with their effects. Thus, the essential oil components of the lemon verbena are used in aromatherapy. In the treatment of nervous restlessness conditions and stress-related exhaustion, inter alia, when orally ingested as a tea, they serve as agents used in delay in onset of sleep, or minor digestion complaints.

Wannmacher et al. examined the postulated sedative and anxiolytic effects of lemon verbena tea formulations but could not find any significant effect in a human randomized double-blind parallel-group study on 40 healthy subjects (Wannmacher L. et al. —Plants employed in the treatment of anxiety and insomnia: II. Effect of infusions of *Aloysia triphylla* on experimental anxiety in normal volunteers.

Fitoterapia 1990; 61: 449-453). Thus, a simple aqueous fluid extract having a low proportion of essential oil did not sufficiently show a significant effect on the central nervous system (CNS).

Under the name of "Planox L", aqueous extracts of lemon verbena are described to which an anti-aging effect is attributed. This is said to be based on anti-oxidative and anti-inflammatory properties on epithelial cells, which preferably occur in the skin and intestinal region.

CN 107397011 (A) describes a Chinese herbal tea with a mixture of nine different plants, which is described to be refreshing. It is an aqueous extract. The component described as verbena is common vervain, not lemon verbena.

CN 102309622 (B) relates to individual glycosides from *Verbena* for use in cerebral ischemia. From paragraph [0007], it can be seen that the plant in question is common vervain (*Verbena officinalis*).

Erping Xu et al., Saudi Pharmaceutical Journal 25 (2017) 660-665, describes the testing of different plant components in cerebral ischemia. Inter alia, a formulation of *Verbena* total glycosides is tested. The composition of the mixture of substances is unclear. The glycosides originate from "verbena", which is the English term for the common vervain, rather than from lemon verbena.

Carpinella et al. in Phytotherapy Research 24 (2010), 259-263, describes purely ethanolic extracts from 73 different plants, which are subsequently separated into aqueous and organic fractions. The measuring system applied, i.e., "acetylcholine esterase inhibition", is used as a screening for diseases such as Alzheimer's disease.

DE 10 2007 052 223 A1 relates to extracts from *Verbena officinalis* L., i.e., common vervain; see paragraph [0002].

WO 2005/058338 A1 relates to extracts from lemon verbena. A depletion of essential oils is not described for the thus obtained extracts.

For an extract prepared by an aqueous route, prepared by lyophilization and being free of essential oil, Ragone et al. also postulate a sedating and anxiolytic effect, which is to be mediated through a $GABA_A$ receptor affinity. In an open-field test, this was examined on mice, and a heart-sparing negatively inotropic activity was shown and demonstrated on an isolated rat heart (Ragone M I, Sella M, Pastore A, Consolini A E. Sedative and Cardiovascular Effects of *Aloysia citriodora* Palau, on Mice and Rats. Latin American Journal of Pharmacy (Lat Am J Pharm) 2010; 29(1): 79-86.). Thus, a CNS activity could also be demonstrated for a dry extract prepared by an aqueous route and having no essential oil fraction.

This was confirmed by examinations by Veisi et al., who also prepared dry extracts by an aqueous route with thermal drying and administered them orally to rats. Thus, no anxiolytic effects were found in an elevated-plus maze from 10 mg of extract/kg of body weight (Veisi M, Shahidi S, Komaki A, Sarihi A.: Assessment of aqueous extract of Lemon verbena on anxiety-like behavior in rats. J Pharm Negative Results 2015; 6: 37-9), but an anxiety-promoting effect ("anxiety-like behavior") was found.

Ceuterick et al. investigate in the evaluation of the ethnobotanical use of medicinal plants among Colombians in London, including lemon verbena with anxiolytic, sedative and anti-depressive applications (Ceuterick M., Vandebroek I., Torry B., Pieroni A. —Cross-cultural adaptation in urban ethnobotany: The Colombian folk pharmacopoeia in London, Journal of Ethnopharmacology 120 (2008) 342-359). In terms of the substances, the use of tea from fresh or dried leaves and thus purely aqueous extracts was always described. The influence on the range of components of a lemon verbena leaf extract of changing the production method (e.g., the extractant) in correlation with a property influencing the CNS has not been described to date. Also, there are no further analytical hints to the effectiveness-related groups of components in a CNS-influencing property.

None of the documents shows effects of extracts prepared with aqueous ethanol from lemon verbena that are virtually free of essential oils.

It has been the object of the present invention to find further fields of application for lemon verbena. This object is achieved by extracts from leaves of lemon verbena (*Aloysia citriodora*) for use in the treatment and prevention of neuronal or cerebral disorders.

The invention describes the standardized preparation of extracts from the leaves of lemon verbena (*Aloysia citriodora*) and their effects in correlation with a specific CNS-mediated clinical picture exerted by influencing neurotransmitters. Thus, the former fields of application can be broadened to include the range of indications of attention deficit disorder, and/or the increase of cognitive performance as a preliminary stage of Alzheimer's disease.

The attention deficit hyperactivity disorder (ADHD) is a psychic disorder whose onset is in childhood, characterized by problems with attentiveness and impulsiveness, and often also hyperactivity. Up to ten percent of all children in Europe show symptoms of an ADHD (boys significantly more frequently than girls). The symptoms may persist to the adult age with different intensity. In from 30% to 70% of the adolescents suffering from ADHD, the disorder persists to the adult age (persistence).

In the adult age, hyperactivity takes an altered character, its effects being an increased inner restlessness. ADHD sufferers often also show various other psychic disorders, e.g., depression, anxiety disorders, and disorders of self-perception, self-esteem, and social phobias. According to the current evidence, the attention deficit hyperactivity disorder is a multifactorially caused disorder condition with a hereditary disposition, which favors the manifestation of the disease.

On a neurobiological level, ADHD is often explained by a striatofrontal dysfunction. Affected areas of the brain, more precisely the frontal brain lobe, are those in which the motivation, cognition (conversion of information), emotion and movement behavior are regulated, or their interaction coordinated. Since areas of the so-called striatum (part of the basal ganglia belonging to the cerebrum) are affected in addition to the frontal brain lobe, physicians speak of a striatofrontal dysfunction.

Prevalence estimates in Germany from 2009 to 2014 support the increase in frequency of ADHD diagnoses from 5.0% to 6.1% in zero to seventeen year old patients, and from 0.2% to 0.4% in 18 to 69 year old patients. It is one of the most widespread chronic diseases in children and adolescents. It occurs more frequently in boys as compared to girls, and also more frequently in children as compared to adolescents. Boys of about 9 years of age represent the maximum with 13.9% affected (Bachmann C J, Philipsen A, Hoffmann F: ADHD in Germany: trends in diagnosis and pharmacotherapy—a country-wide analysis of health insurance data on attention-deficit/hyperactivity disorder (ADHD) in children, adolescents and adults from 2009-2014. Dtsch Ärztebl Int 2017; 114: 141-8. DOI: 10.3238/arztebl.2017.0141).

While the prescription of ADHD medications increased for adults with an ADHD diagnosis (the most prescribed drugs being methylphenidate, followed by atomoxetine and lisdexamfetamine), the prescription rate decreased for children and adolescents. The need for alternative drugs is very great.

For the medication of ADHD, stimulants influencing the dopamine metabolism in the brain are primarily employed. These include methylphenidate and amphetamine derivatives (DL-amphetamine), which have been used since about the middle of the last century. About ⅔ of the affected respond to this medication. Further, anti-depressive agents influencing the dopamine or noradrenaline metabolism may also be employed for treatment.

One cause of ADHD is an anomaly in the signal processing in the brain. This disorder is based on a deficiency or reduced effectiveness of the neurotransmitters noradrenaline and dopamine. For example, the attentiveness is controlled through noradrenaline, and the motivation through dopamine. Correspondingly, the result of disturbed signal processing is difficulties of affected persons in concentrating on one thing at a time, and in filtering external stimuli based on their significance or insignificance, i.e., easy distractibility and overstimulation. In addition, a participation of the neurotransmitter serotonin in ADHD has been demonstrated. Serotonin controls the impulsiveness and accordingly, when in disorder, can lead to increased impulsiveness, low frustration tolerance, and a poor behavior adaptation of affected persons to the respective circumstances.

Methylphenidate, which is the substance employed most frequently today for the therapy of the attention deficit hyperactivity disorder, inhibits the reuptake of dopamine and noradrenaline in the presynapses and thus increases their concentration in the synaptic cleft. This results in an increased signal density on the receptor and, inter alia, in an increase of the sympathetic tone. Thus, substances that inhibit the selective reuptake of noradrenaline and dopamine (and also slightly that of serotonin) are promising candidates for the treatment of ADHD. However, this active substance is also characterized by an extensive potential for side effects. The following frequently occurring side effects are known: rhinopharyngitis, reduced appetite, moderately reduced increase in weight and size (in extended application to children), mental imbalance, anxiety, depression, irritability, cardiac arrhythmia, etc.

Clinical experience indicates that methylphenidate can enhance the symptoms of behavioral and thought disorders in psychotic children. There is no treatment recommendation for children below 6 years of age. The side effects are seen most likely in long-term administration. Chronic improper use may even lead to methylphenidate losing its effect (development of tolerance), and to psychological dependence.

Cognition (conversion of information) is a measurable criterion within striatofrontal dysfunction. Even though "cognition" is often used with varying meanings, "cognition" means thinking in a comprehensive sense. Although many cognitive processes in humans are conscious, "cognition" and "consciousness" do not have the same meaning. Certain processes in humans may be unconscious and yet cognitive. An example of this is unconscious learning. The cognitive abilities of a human include, for example, attentiveness, memory, learning, creativity, planning, orientation, imagination, argumentation, self-observation, willingness, faith, and some more. Cognitive abilities are examined by different sciences, such as psychiatry, psychology, philosophy, and the neurosciences.

Therefore, cognitive performance is a complex process, which can be quantified with measurable parameters of brain performance. The ability to learn includes both memorizing (duration and amount of memorized input), and the influence on responsiveness, the ability to perform logical operations (fast and correct), or capacity for spatial thinking, e.g., in a phase of orientation under new and altered conditions. Disorders of such cognitive performance are described, inter alia, by the syndrome MCI (mild cognitive impairment). MCI represents a specific condition of the age-related reduction of cognitive functions and abilities. In healthy people, testing of MCI may be considered a preindicator of later dementia.

Surprisingly, it has now been found that extracts from the leaves of lemon verbena (*Aloysia citriodora*) had highly inhibiting properties on the reuptake of noradrenaline and dopamine and inhibiting serotonin in synaptosomes from rat cortex. In addition, the suitability in ADHD as found through in vitro results could be confirmed by in vivo experiments with nematodes, by means of EEG recordings in mice, and additionally in a behavior model (Morris water maze) in mice.

It was newly found that, in particular, the field of cognition is advantageously supported by the oral administration of hydroethanolic extracts from lemon verbena.

It has also been found that the regular dosed intake of extracts from lemon verbena, such as drinking an instant formulation, showed a significant treatment effect in ADHD patients.

Thus, the invention relates to the use of extracts from the leaves of the species *Aloysia citriodora* (or its synonymous designations) for the treatment of ADHD and/or cognition and/or mild cognitive impairment, and/or stress-related exhaustion conditions/stress disorders.

Diseases that can be treated or prevented according to the invention include somatoform diseases (burnout syndrome), acute and posttraumatic stress disorders, chronic fatigue syndrome; nervous restlessness (mental stress), anxiety and depression as symptoms of neurotic disorders, and stress symptoms, such as tiredness and weakness.

Preferably, said neuronal disorder is not a neurodegenerative disease associated with accumulated proteins/peptides, in particular, it is not Alzheimer's or Parkinson's disease.

The invention also relates to the use of extracts from the leaves of the species *Aloysia citriodora* (or its synonymous designations) for preparing a medicament for the treatment of ADHD.

The invention further relates to the use of extracts from the leaves of the species *Aloysia citriodora* (or its synonymous designations) for preparing a therapeutic agent for improving the cognitive performance and/or mild cognitive impairment.

The invention also relates to the use of extracts from the leaves of the species *Aloysia citriodora* (or its synonymous designations) for preparing a therapeutic agent for use in nervous restlessness (mental stress).

In the following, the invention is explained by means of preferred embodiments and individual Examples, which also relate to preferred embodiments. In preferred uses according to the invention, dried and cut leaves of lemon verbena that meet the quality criteria of the Ph. Eur. monograph are employed for the above-mentioned purposes. In further preferred embodiments of the invention, extracts prepared from dried leaves of lemon verbena Ph. Eur. are employed. Alternatively, it is also possible to use leaves and extracts from leaves of lemon verbena together.

When extracts from the leaves of lemon verbena are used, these are alcoholic-aqueous extracts, for example. In this context, "alcohol" means lower (C1 to C4) alcohols that are all miscible with water.

Preferred solvents include methanol, ethanol, isopropanol and mixtures thereof, in which ethanol is particularly preferred. The volume ratio of the alcohol-water mixture for obtaining the extracts from the leaves of lemon verbena may vary within a broad range. It is preferably from 99:1 to 1:99% by volume, more preferably from 70:30 to 30:70% by volume, most preferably from 55:45 to 45:55% by volume (based on the ratio of alcohol to water in the whole mixture used for extraction). Preferred ratios include from 10:90 to 70:30, or from 10:90 to 60:40, or from 20:80 to 70:30, or from 20:80 to 60:40, respectively as % by volume and as alcohol:water. Preferably, a mixture of ethanol and water is employed as an extractant, wherein mixing ratios of from 70:30 to 30:70% by volume, especially from 60:40 to 40:60% by volume, or from 55:45 to 45:55% by volume, are particularly suitable. In other embodiments, particularly suitable extractants include mixtures of water with contents of from 10:90 to 30:90% by volume. Preferred ratios are from 10:90 to 70:30, or from 10:90 to 60:40, or from 20:80 to 70:30, or from 20:80 to 60:40, respectively as % by volume and as ethanol:water. All values in % by volume are based on the volume at 21° C.

However, other mixtures, for example, mixtures of water with organic solvents, such as ketones or organic acids, may also be employed as extractants. The characteristic of the selected organic solvents is the fact that, after the process of extraction, they were removed from the enriched extract by distillation, sublimation, or freezing out.

In further preferred embodiments of the invention, the extracts prepared by means of the exemplary extractants mentioned above are not used as such but subjected to a further purification as a primary extract. Such treatment steps may be:
- the enzymatic treatment of aqueous extracts in the presence of cell components;
- the removal of essential oil fractions and volatile organic components by distillation, preferably azeotropic distillation;
- the removal of essential oil fractions and lipophilic components, such as plant resins and chlorophyll, by a liquid-liquid purification using aliphatic hydrocarbons;
- the enrichment of polar valuable components by a liquid-liquid extraction with n-butanol or ethyl acetate;
- the enrichment of polar valuable components by a liquid-solid extraction on solid phases, such as organic adsorber polymers.

The performing of the stated purification steps and the recovery of extract fractions obtained from the stated primary extracts may be effected in any way as known as such by those skilled in the art, and therefore, there is no need for any further explanation here.

Further, in other preferred embodiments according to the invention, extracts from the leaves of lemon verbena and/or fractions prepared from such extracts can be used singly or in combinations with one another. Similarly, it is also preferred according to the invention to use extracts from the leaves of lemon verbena and/or fractions prepared from such extracts singly or in combinations with one another and in combination with chemical-synthetic substances, e.g., non-selective monoamine reuptake inhibitors (NSMRIs), selective serotonin reuptake inhibitors (SSRIs), selective noradrenaline reuptake inhibitors (NARIs), serotonin-noradrenaline reuptake inhibitors SNRIs), dopamine reuptake inhibitors (DRIs), selective noradrenaline-dopamine reuptake inhibitors (NDRIs), or MAO inhibitors.

The use of the invention according to the embodiments as described above may be a use in the form of a pharmaceutical formulation. As such, it may take usual dosage forms known as such to those skilled in the art, comprising a certain concentration of lemon verbena extracts in a form that enables a dosed administration in usual pharmaceutical dosage forms. In a way known to those skilled in the art, the dosage form depends on the route of administration (oral, intravenous, intramuscular, nasal), and may be a solid, semisolid, liquid, sprayed, gaseous or other form allowing administration on the desired route. In addition, the use according to the invention with one of the above-mentioned dosage forms may also be a use as a food supplement.

The following Examples of a preferred embodiment explain the invention.

PREPARATION AND CHARACTERIZATION OF EXTRACTS FROM LEMON VERBENA LEAVES

Figure 1:
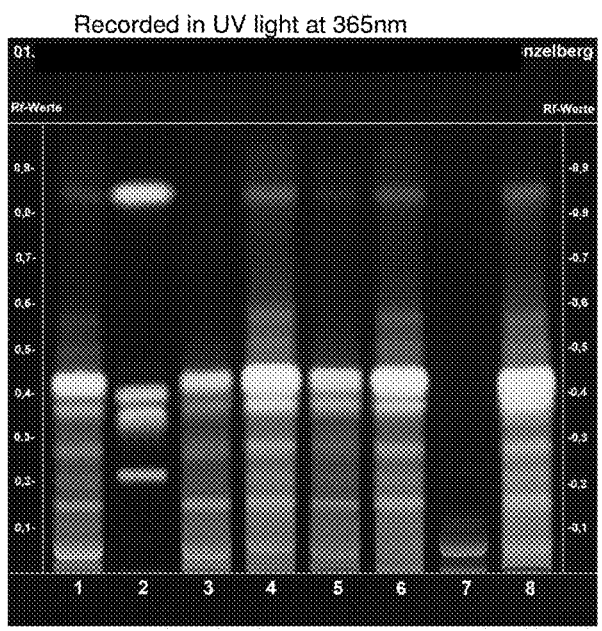
FIG. 1 shows a thin-layer fingerprint comparison on flavonoid substances (yellow) and CQA compounds (light blue) using as examples extract fractions from lemon verbena vs. primary extract 50% v/v EtOH. Identical native fractions of the extracts were applied.

Example 1: Extraction with Water 1500 g of lemon verbena leaves (folia *Aloysia citriodora*) is admixed with 15 liters of osmosis water twice at 80° C. and extracted for 8 hours with occasional stirring (moved maceration). The mixture is allowed to stand over night for cooling. The eluate is separated from the extracted starting material and filtered clear through a cellulose filter. The filtrate is evaporated on a plate evaporator to form a viscous spissum extract. The evaporation process is repeated twice after the addition of water in order to remove all volatile components. To 622 g of a spissum extract evaporated to 71.4% solids, 190 g of the drying additive maltodextrin is added. This 70% native extract formulation is spray-dried to form a beige powder (temperature at the spray head: 185° C., outlet temperature from the spray tower: 105° C.). The resulting extract formulation is a beige-colored powder characterized by a fraction of essential oil of <0.01%, a content of 0.06% flavonoids, and 1.8% verbascoside.

Example 2: Extraction with 20% by Volume Ethanol in Water 1700 g of lemon verbena leaves (folia *Aloysia citriodora*) is admixed with 10 liters of 20% (v/v) ethanol twice at 50°

C. and percolated for 8 hours (moved extraction). The mixture is separated from the extracted starting material and filtered clear through a 40 μm cellulose filter. The filtrate is freed from its ethanol fraction in a Sambay evaporator and evaporated to form a homogeneous spissum extract. By repeatedly adding water and evaporating it again under a reduced pressure, the extract is freed from volatile components. To 611 g of a spissum extract evaporated to 69.5% solids, 182 g of drying additives is added. This 70% native extract formulation comprises 28% maltodextrin and 2% Aerosil (fumed silica), and is dried in a vacuum drying oven at 45° C. The extract is subsequently ground in a sieve mill with a 0.315 mm sieve to form a homogeneous beige-brown powder. The resulting extract formulation is characterized by a fraction of essential oil of <0.01%, a content of 0.06% flavonoids, and 4.3% verbascoside.

Example 3: Extraction with 50% by Volume Ethanol in Water 1700 g of lemon verbena leaves (folia *Aloysia citriodora*) is admixed with 10 liters of 50% (v/v) ethanol twice at 50° C. and percolated for 8 hours (moved extraction). The mixture is separated from the extracted starting material and filtered clear through a 40 μm cellulose filter. The filtrate is pre-evaporated on a plate evaporator and finally evaporated on a rotary evaporator under vacuum at 45° C. to form a solvent-free spissum extract. By adding water, the evaporation process is repeated twice in order to remove all volatile components. To 750 g of a spissum extract evaporated to 64.3% solids, 206 g of drying additives is added. This 70% native extract formulation comprises 28% maltodextrin and 2% Aerosil (fumed silica), and is dried in a vacuum drying oven at 45° C. The extract is subsequently ground in a sieve mill with a 0.315 mm sieve to form a homogeneous brown powder. The resulting extract formulation is characterized by a fraction of essential oil of <0.01%, a content of 0.51% flavonoids, and 11.6% verbascoside.

Example 4: Extraction with 96% by Volume Ethanol 1500 g of lemon verbena leaves (folia *Aloysia citriodora*) is admixed with 15 liters of 96% (v/v) ethanol twice at room temperature, 20° C., and extracted for 8 hours with occasional stirring (moved maceration). The mixture is separated from the dry extract and filtered clear through a 40 μm cellulose filter. The clear greenish filtrate is evaporated on a plate evaporator to form a spissum extract. By adding water, the evaporation process is repeated twice in order to remove all volatile components. To 190 g of a spissum extract evaporated to 65.8% solids, 54 g of drying additives is added. This 70% native extract formulation comprises 20% maltodextrin and 10% Aerosil. The increasing silica content is necessary for binding and drying the increased chlorophyll fractions with this lipophilic extractant. Finally, the material is dried in a vacuum drying oven at 45° C., and ground in a ball mill to form a powder. The resulting extract formulation is a green-brown powder characterized by a fraction of essential oil of <0.1%, a content of 1.70% flavonoids, and 19.6% verbascoside.

Characterization of the Extracts

TABLE 1

Extract characterization as a function of the extraction solvent

| Extract No. | Extractant | Yield of native extracted material | Drug-to-extract ratio | Character of extractant | Appearance of 70% native extract formulation |
| --- | --- | --- | --- | --- | --- |
| 1 | water | 29.6% | 3.4:1 | polar, highly hydrophilic; water-soluble | beige powder |
| 2 | EtOH 20% (v/v) | 25.0% | 4.0:1 | polar, hydrophilic; water-soluble | beige-brown powder |
| 3 | EtOH 50% (v/v) | 28.4% | 3.5:1 | polar, partially hydrophilic; partially water-soluble | brown grain |
| 4 | EtOH 96% (v/v) | 8.3% | 12.0:1 | non-polar, lipophilic maximum; not water-soluble | green-brown grain |

The drug-to-extract ratio represents the concentration factor; arithmetically, it is the reciprocal of the yield of native extracted material.

All comparable mixtures were generated from one and the same batch of lemon verbena leaves. This batch corresponded to the Ph. Eur. grade (content of essential oil: 0.5%; content of acteoside: 5.6%). All preparation variants resulted in extract formulations free of essential oils having different solution properties, appearances, and different contents of polar components, such as the flavonoids or verbascoside (phenylethanoid). The determination of flavonoids was performed as a group determination by UV spectroscopy by analogy with the Ph. Eur. method with birch leaves with the reference substance hyperoside. Verbascoside is a synonym of acteoside, whose determination was effected by analogy with the acteoside HPLC method for lemon verbena leaves by analogy with Ph. Eur. 1834.

Example 5: Determination of the Properties of Influencing the Neurotransmitters Noradrenaline, Dopamine and Serotonin by Extracts from Lemon Verbena Leaves Freshly isolated synaptosomes from rats were used according to Perovic and Müller [Perovic S, Müller W E, 1995, Arzneimittelforschung 45; 1145-1148] for a dopamine reuptake test, and a serotonin reuptake test, and a noradrenaline reuptake test. [$^3$H]-dopamine, [$^3$H]-noradrenaline and [$^3$H]-serotonin, respectively, served as the ligands. The test substance was incubated with the synaptosomes and the corresponding ligand for 15 min at 37° C. in the dark. The samples were then transferred to GF/C filter plates, and washed cold twice, and dried, before the filter-bound radioactivity was measured with a microtitration plate counter (Microbeta, Wallac, Finland). For determining the 100% reuptake, the experiment was performed without test substances. The measured value for incubation with corresponding inhibitors (GBR12909 in the dopamine reuptake inhibition, protriptyline in the noradrenaline reuptake inhibition, and imipramine hydrochloride for the serotonin reuptake inhibition) was considered as a 0% uptake. For a first screening for the suitability of the extracts for ADHD, Sommer et al. (Sommer et al.: Ein pflanzliches Arzneimittel im Vergleich zu Methylphenidat: Ein alternativer Weg in der zukünftigen Behandlung von ADHS?, GPT poster contribution to the GPT Phytokongress in September 2017 in Münster, Germany, Zeitschrift für Phytotherapie Issue S 01 •Volume 38•DOI: 10.1055/s-007-34868) recommend a mean reuptake inhibition within a range of <50 μg/ml for dopamine or noradrenaline for a combination medicament with about 20 μg/ml as a potent example. Markowitz et al. found a significantly weaker effect for serotonin and confirmed the effects for noradrenaline and dopamine (Moskowitz et al.: A Comprehensive In Vitro Screening of d-, l-, and dl-threo-Methylphenidate, Journal of child and adolescent Psychopharmacology 16, 2006, 687-698).

TABLE 2

Neurotransmitter reuptake inhibition by extracts from lemon verbena leaves as compared to methylphenidate

| Sample name | DER native | Serotonin (IC$_{50}$ μg/ml) | Noradrenaline (IC$_{50}$ μg/ml) | Dopamine (IC$_{50}$ μg/ml) |
|---|---|---|---|---|
| Extract No. 1 (water) | 3.4:1 | 308 | 23 | 82 |
| Extract No. 2 (20% EtOH) | 4.0:1 | 16 | 4 | 6 |
| Extract No. 3 (50% EtOH) | 3.5:1 | 128 | 21 | 30 |
| Extract No. 4 (96% EtOH) | 12.0:1 | 43 | 12 | 20 |
| Methylphenidate (positive control) | | not determined | 0.050 (Sommer et al.) | 0.114 (Sommer et al.) |
| | | 4.310 (Markowitz et al.) | 0.052 (Markowitz et al.) | 0.260 (Markowitz et al.) |

Surprisingly, a very good potential for inhibiting the reuptake of the three neurotransmitters was found for all four tested lemon verbena extracts. The highest potential is found for noradrenaline, where all four extracts show a very potent reuptake inhibition of <25 μg/ml. Also, all four extracts are capable of inhibiting the reuptake of dopamine in a dose-dependent way. The three hydroethanolic extracts show good IC50 values of max. 30 μg/ml; the aqueous extract still shows a good effect but falls behind the hydroethanolic extracts by a factor of at least 2.6. A similar picture is seen for the influencing of serotonin. Here too, an aqueous extract shows the least activity. The hydroethanolic extracts show a clear dependence on the extractant from a good (extract 4) and very good (extract 2) to medium activity (extract 3). All in all, however, the extracts show a significantly higher activity in serotonin reuptake inhibition as compared to methylphenidate. Thus, the activity ratio of serotonin to noradrenaline is a factor of 86 for methylphenidate, while extract 2 or extract 4 have factors of about 4.1 in this case. Thus, surprisingly, a basically similar activity profile for the influencing of noradrenaline and dopamine is found for the extracts from lemon verbena leaves, and additionally an improved influencing of serotonin. Considering the three most important neurotransmitters tested, the extracts are very suitable candidates for the treatment of ADHD.

Further, if the mentioned results are taken in relation to the concentration factors (native DER value) and to the galenic properties of the extracts, a preferred range is obtained for medium polar extracts, such as extract No. 2 or 3. Here, as compared to pure water as an extractant, there is a significant improvement of the pharmacological properties while the enrichment is almost identical and the galenic properties are similar. If this is compared to extract No. 4, a highly lipophilic extractant with 96% v/v EtOH, the degree of enrichment is higher by a factor of 3 for extract 4 vs. extract 2, with a DER of 12:1. If the IC$_{50}$ values obtained for the three neurotransmitters are divided by the additional enrichment factor 3, the IC$_{50}$ values are obtained for an arithmetically similar total enrichment from the dried leaves, here a native DER of 4:1.

| Neurotransmitter | IC$_{50}$ for extract 2 (DER 4:1) | IC$_{50}$ for extract 4 calculated for a DER of 4:1 |
|---|---|---|
| Serotonin | 16 | 14.3 (43/3) |
| Noradrenaline | 4 | 4 (12/3) |
| Dopamine | 6 | 6.7 (20/3) |

This numerical comparison shows that lipophilic extracts with pure ethanol (extract 4) include the effectiveness-codetermining components of the starting material on the same level as a medium polar-aqueous-ethanolic extract (extract 2), if they are based on the same extract yields (here DER=4:1). There are virtually identical results for all three neurotransmitters considering a relative gain error of 5-10%.

This is not an advantage even if the economic efficiency with a higher extraction price (a higher material usage is necessary: 12 times vs. 4 times) is considered. Further, worse galenic properties with respect to appearance (green-brown), handling (hygroscopic dry extract) and solubility (virtually insoluble in aqueous medium) result for extract No. 4 as compared to extracts Nos. 2 and 3. This is caused by the transfers of cuticular wax and chlorophyll fractions from leaves, which is favored by the extractant 96% v/v EtOH. These problems can be avoided when using maximally 50% or 60% (v/v) ethanol.

Further Purification

Proceeding from a primary extract obtained with 50% v/v ethanol, the further separation into strongly lipophilic, non-polar and polar hydrophilic components was performed in terms of production technology. Thus, a total of six subfractions were obtained using known separation techniques, such as liquid-liquid partition, liquid-solid phase separation, and reprecipitation in ethanol. These were examined for their recoveries (=enrichment factors), typical components and their fingerprint by thin-layer chromatography (see FIG. 1).

Example 6: Liquid-Liquid Extraction

A primary extract from 50% v/v ethanol, prepared by analogy with Example 3, was redissolved in demineralized water to 10% dry matter, and permanently stirred. Thus, tree additions with one third each of the volume of the primary solution of n-butanol were performed, followed by intense stirring. Subsequently, phase separation in a separating funnel was performed. The three butanol phases combined were evaporated on a rotary evaporator under vacuum until free of solvent. Subsequently, this extract phase of 70% native/30% drying additives (28% maltodextrin and 2% silicas) was dried in a vacuum drying oven at 45° C., and then ground to a homogeneous powder. Similarly, the remaining aqueous phase was processed and dried as 70% native extract powder.

Example 7: Reprecipitation in Ethanol

A primary extract from 50% v/v ethanol, prepared by analogy with Example 3, was added in portions to 96% v/v ethanol until a total of 10% by weight dry matter was present in dissolved form. After 60 min of stirring, the solution was left to stand in a cold place at 6° C. for 24 hours. Hydrophilic substances precipitated.

After separating the upper ethanol phase by decanting, the precipitate was taken up in water. The mixture was evaporated on a rotary evaporator under vacuum until free of solvent. Subsequently, this extract phase of 70% native/30% drying additives (28% maltodextrin and 2% silicas) was dried in a vacuum drying oven at 45° C., and then ground to a homogeneous powder. The ethanolic supernatant was also evaporated on a rotary evaporator under vacuum until free of solvent, and also dried as 70% native extract powder.

Example 8: Liquid-Solid Distribution

A primary extract from 50% v/v ethanol, prepared by analogy with Example 3, was redissolved in demineralized water to 10% dry matter, and stirred for 30 min. The solution was left to stand in a cool place over night for 12 hours. A small fraction of the extract precipitated as an insoluble solid. It was filtered off through a folded filter and discarded. The clear eluate was placed on a glass column filled with an adsorber of the type XAD-7HP. The charged amount of dissolved native extract was 25% by weight of the dry weight of the adsorber. The adsorber is so selective that it binds polar medium-sized substances like flavonoids, phenols etc., and allows smaller molecules like sugars, salts and amino acids to pass. The filtering effect of the adsorber retains substances in the interior of the adsorber. These were washed off by elution with two bed volumes of 96% v/v ethanol. The ethanolic eluate obtained was evaporated on a rotary evaporator under vacuum until free of solvent. Subsequently, this extract phase of 70% native/30% drying additives (28% maltodextrin and 2% silica) was dried in a vacuum drying oven at 45° C., and then ground to a homogeneous powder. Also, the previously collected aqueous phase, which had passed the adsorber, was processed and dried to a dry extract powder with 70% native fraction and 30% additives.

TABLE 3

Extract characterization of six extract fractions of lemon verbena
Primary extract: Extr. *Aloysiae citriodor.* e herb. spir. spiss.
(50% v/v EtOH), enrichment factor = 4:1 (DER native)
(5.88% verbascoside/0.54% CQA compounds/4.65% flavonoids)

| Liquid-liquid partition Example 6 | | Reprecipitation in EtOH Example 7 | | Separation on adsorber resin Example 8 | |
| --- | --- | --- | --- | --- | --- |
| Water phase Extract No. 5 | n-butanol phase Extract No. 6 | Water phase Extract No. 7 | EtOH phase Extract No. 8 | Water phase Extract No. 9 | EtOH phase Extract No. 10 |
| 66% rel. quant. distribution | 34% | 50% | 50% | 69% | 31% |
| 6:1 enrichment | 11.8:1 | 8:1 | 8:1 | 5.8:1 | 12.9:1 |
| 1.24% flavonoids | 11.64% | 1.61% | 9.35% | 0.01% | 14.01% |
| 1.52% Verbascoside | 17.01% | 2.07% | 11.92% | 0.01% | 20.02% |
| 0.31% CQA compounds | 1.20% | 0.54% | 0.82% | 0.02% | 1.42% |
| Thin-layer chromatography caffeic acids + flavonoids enriched | caffeic acids + flavonoids enriched | caffeic acids + flavonoids enriched | caffeic acids + flavonoids enriched | all distinctive zones are lacking! | caffeic acids + flavonoids enriched |

TABLE 4

Neurotransmitter reuptake inhibition by extract fractions from lemon verbena leaves as compared to the 50% v/v EtOH primary extract

| Sample name | Serotonin ($IC_{50}$ µg/ml) | Noradrenaline ($IC_{50}$ µg/ml) | Dopamine ($IC_{50}$ µg/ml) |
| --- | --- | --- | --- |
| Primary extract No. 3 | 128 | 21 | 30 |
| Extract No. 5 (water phase) | 234 | 6 | 82 |
| Extract No. 6 (butanol phase) | 17 | 1 | 14 |
| Extract No. 7 (water phase) | 54 | 7 | 43 |
| Extract No. 8 (ethanol phase) | 26 | 8 | 15 |
| Extract No. 9 (water phase) | 363 | 25 | 191 |
| Extract No. 10 (ethanol phase) | 44 | 5 | 9 |

Also considering the analytical data relating to the components, the fractionations demonstrate that an enrichment towards medium polar to polar-lipophilic substances can enhance the activity effects. With the enrichment of the substance groups flavonoids, caffeoylquinic acids (CQA compounds) and verbascoside, the reuptake inhibitions increase for all three neurotransmitters tested.

This can be seen particularly well in the extracts Nos. 9 and 10, which resulted from the adsorber resin separation. The adsorber selectively separated the target substances from the water phase (extract No. 9), whereby its activity was clearly reduced as compared to the primary extract for serotonin and dopamine. The fact that noradrenaline was affected at about the same order of magnitude also shows that the overall extract determines the activity, rather than only individual marker substances/groups of substances. By implication, the ethanolic extract phase from the adsorber (extract No. 10) could achieve a concentration by a factor of 3.2 merely in terms of production technology (12.9 for fractionation vs. 4.0 for primary extract). The overall influence on the neurotransmitters improved precisely by about this order of magnitude.

Taking the extracts Nos. 7 and 8 (reprecipitation in ethanol) as examples, the fractionations also show that if the relative quantitative distribution is at 50% each and no difference in the degree of enrichment can be seen, then also approximately equal pharmacological activities result. Here too, despite the different distribution of some analytical marker substances (flavonoids, verbascoside), it is found that although these contribute to the effect, they are by no means the sole active substances. It all depends on the method of extract preparation. Also as compared to the primary extract, this Example again supports the influencing of all three neurotransmitters tested herein by lemon verbena extracts.

In view of these positive in vitro data available, the question arises to what extent this can be also demonstrated in vivo. A suitable model for this is the nematode *C. elegans*. *Caenorhabditis elegans* is a nematode that is being explored as a model organism mainly in developmental biology and genetics. An important reason for this is that, despite only having almost 1000 somatic cells, it has more than 20,000 genes (human: almost 40,000), many of which have similar functions as in mammals. Almost half of all proteins encoded in the worm's genome have homologues in *Homo sapiens*, including a wide variety of known human disease genes. Thus, it is a representative model organism with regard to metabolization, targeted gene expression, and neuronal behavior. The complete nervous system of the nematodes consists of about 300 neurons and is constituted of 2 independent parts: a larger somatic, and a smaller pharyngeal, nervous system. The nematodes use acetylcholine, glutamate, GABA (γ-amino-butyric acid), and biogenic amines, such as serotonin and dopamine, as neurotransmitters.

*C. elegans* lives in the soil of moderate climate zones, where it feeds on bacteria. The animals reach lengths of about 1 mm and have a transparent cuticula. *C. elegans* has a short lifespan of about 15 to 20 days (depending on the temperature and amount of feed). They can be cultivated in a well reproducible manner by placing *Escherichia coli* bacteria as their feed on agar plates. Depending on the problem, transgenic worms whose conversion products with defined substances can be detected directly through fluorescence measurements or by behavioral tests are selectively employed.

Example 9: Protection of Dopaminergic Neurons from 6-OHDA-Induced Degeneration

6-Hydroxydopamine (6-OHDA) damages dopaminergic neurons, which is used in different animal models. The transgenic *C. elegans* strain BZ555 expresses green fluorescent protein in dopaminergic neurons. Thus, the 6-OHDA-induced neurodegeneration or the reduction thereof can be quantified by fluorescence microscopy. The worms were exposed to 50 mM 6-OHDA, which reduces the fluorescence intensity of the neurons because of the degeneration thereof. Bupropione, a selective noradrenaline and dopamine reuptake inhibitor (NDRI), serves as the positive control. Through the inhibition of the noradrenaline (NA) or dopamine (DA) transporters (reuptake), bupropion prevents the neurotoxin 6-OHDA from getting into and damaging the neurons. Treatment with 600 μg/ml of a lemon verbena extract from 50% ethanol according to Example 3 resulted in an about 20% higher fluorescence intensity (protective function) as compared to the negative control.

TABLE 5

Influence of lemon verbena extract (50% v/v EtOH) on 6-OHDA-induced degeneration in nematodes

| Treatment | Untreated worms | Worms + 6-OHDA (negative control) | Worms + 6-OHDA + bupropion 100 μg/ml (positive control) | +6-OHDA + *A. citriodora* extract 600 μg/ml |
|---|---|---|---|---|
| Fluorescence intensity [% of untreated group] | 100.0 ± 2.6 | 34.3 ± 4.3 | 68.2 ± 7.7 ($p < 0.05$) | 43.1 ± 5.0 ($p = 0.07$) |

The damaging of neurons with 6-OHDA in an animal model is a generally recognized experimental set-up for ADHD (Kostrzewa R M et al.: Pharmacological models of ADHD; J Neural Transm (Vienna) 2008; 115: 287-98). The positive control confirms this in the *C. elegans* model employed here. The *A. citriodora* extract according to the invention, like the positive control, has been reported to inhibit the reuptake of NA and DA (see Example 5 above). The *A. citriodora* extract according to the invention can reach about ⅓ of the protective function of the positive control.

Example 10: Influence on β-Amyloid-Induced Toxicity in *C. elegans* Model

In order to test the effect on β-amyloid toxicity, the transgenic *C. elegans* strain CL4176, which can express human β-amyloid (Aβ 1-42), was employed. Aβ expression can be induced by increasing the temperature. Age-synchronized and treated worms were incubated at 16° C. for 48 hours. After increasing the temperature to 25° C. and incubation for 24 hours, the worms began to get paralyzed because of the toxicity of the Aβ oligomer. The paralysis was evaluated every 2 hours (experimental set-up according to Heiner et al.: *Sideritis scardica* extracts inhibit the aggregation of α-synuclein and β-amyloid peptides in *Caenorhabditis elegans* used as a model for neurodegenerative diseases. Planta Medica 81—PW_127, 2015). Substances that counteract this toxic effect of β-amyloid lead to a slower or later paralysis of the animals. Such substances delay the neurodegeneration, inter alia, in Alzheimer's dementia. The median ($PT_{50}$), which is the time when exactly 50% of the nematodes were paralyzed, was used as a comparative value.

| Treatment | Negative control (no treatment) | +A. citriodora extract 50% EtOH 600 µg/ml | +acteoside single substance in A. citriodora 200 µg/ml |
|---|---|---|---|
| $PT_{50}$ value [hours] | 31.0 ± 0.4 | 32.5 ± 0.9 (p = 0.17) | 32.8 ± 0.3 (p < 0.05) |
| Prolongation of lifespan | reference | +1.5 hours | +1.8 hours |

TABLE 6

Influence of lemon verbena extract (50% v/v EtOH) on β-amyloid-induced toxicity

| Treatment | Negative control (no treatment) | +Sideritis scard. extract 50% EtOH 600 µg/ml positive control according to Heiner et al. |
|---|---|---|
| $PT_{50}$ value [hours] | 33.5 ± 0.5 | 37.0 ± 0.0 (p < 0.001) |
| Prolongation of lifespan | reference | +3.5 hours |

Treatment with the lemon verbena leaf extract (50% v/v ethanol) delayed the β-amyloid-induced paralysis by 1.5 hours. The acteoside, which occurs as an individual substance in this extract, positively contributes to the protective effect (+1.8 hours). A plant extract from *Sideritis scardica* (50% EtOH), which has been reported for its suitability in ADHD (EP 2 229 950 B1), was tested in the same model and used as a positive control and showed a highly significant effect (+3.5 hours).

Example 11: Influence on β-Amyloid-Induced Neuronal Dysfunction (Limited Cognition)

β-Amyloid species can damage neurons and trigger a dysfunction of neuronally controlled behavior. The transgenic *C. elegans* strain CL2355 expresses human β-amyloid on a pan-neuronal level. This leads to cognitive disorders, such as reduced chemotactic movement towards an attractant (benzaldehyde). In the experiments, the chemotaxis index, i.e., the proportion of worms moved towards the attractant on the agar plate, was measured. The control strain CL2122 does not express β-amyloid and shows no behavior disorders; its chemotaxis index was correspondingly high. The experiment was performed in accordance with Heiner et al.

TABLE 7

Influence of lemon verbena extract on neuronal dysfunction

| Treatment | Chemotaxis index |
|---|---|
| CL2355 test strain untreated (negative control) | 0.10 ± 0.04 |
| CL2122 control strain (positive control) | 0.50 ± 0.09 |
| CL2355 + *A. citriodora* extract (50% EtOH) 600 µg/ml | 0.23 ± 0.02 (p < 0.05) |
| CL2355 + acteoside individual substance in *A. citriodora* 200 µg/ml | 0.45 ± 0.02 (p < 0.05) |

Treatment with a lemon verbena leaf extract (50% v/v ethanol) according to the invention showed a significant chemotaxis index that was increased by a factor of 13. The improvement over the untreated test strain was 46%. This is due to a reduced β-amyloid-induced degeneration of the neurons that are important o this cognitive ability. The acteoside, which occurs as an individual substance in this extract, is demonstrably involved in the neuroprotective effect (reached about 88% of the chemotaxis index of the control strain CL2122).

Example 12: Behavior Examinations in a Morris Water Maze (MWM)

According to the animal model "Morris water maze", the increase of the cognitive performance becomes visible especially under an existing stress situation by showing an increase in the learning performance, especially retentiveness. In a round pool filled with muddy water provided with lateral distinctive marks, so-called external cues, test animals, in this case mice, are trained over several days to independently find a hidden platform provided under the water's surface, and to memorize its spatial position. The mice are put into water at an approximate distance from the edge of about 30 cm, whereupon the animals immediately try to reach the saving platform with swimming movements. The advantage of this measuring system, which has been known since the beginning of the 1980's, over conventional simple mazes in animal experiments is the fact that there are no local landmarks, but only global ones, and that the task has a high motivation factor because of the animals' escape behavior. The experiment is mainly directed to the examination of (spatial) learning (recognition and memorization) of the animals under stress conditions, and the measurement of possible influences thereon. The measuring parameters include the time until they find the platform, the distance traveled to there, as well as the relative stay time in the correct quadrant of the pool. These parameters are influenced by the training effect. Thus, the time of meeting and the journey is usually reduced, and the time spent in the quadrant is prolonged. The effect of training can also be influenced by different concentrations of neurotransmitters [Doctoral Thesis, University of Freiburg 2004, Theresa Schweizer: 3,4-Diaminopyridin evozierte Freisetzung von Neurotransmittern aus Hirnschnitten von Ratten: Untersuchungen im Kortex und Hippocampus an alten Ratten, sowie an Ratten mit serotonergen Läsionen hippocampaler Afferenzen und intrahippocampalen Raphé-Transplantaten].

In this test arrangement, 2 groups of 6 mice were studied, inter alia. The first control group was formed by transgenic animals treated with water (strain AD-B6) that due to their genetic disposition manifested in the interval of 50 days after their birth a strong β-amyloid deposition, or they became ill with Alzheimer's disease. The other two control groups consist of transgenic animals (strain AD-B6) that from their d=50 day of life were treated with a solution of a lemon verbena extract according to Example 2 or Example 3. In each case, the dosage was 400 mg of native extract per kg of body weight.

At the age of about 95 days a behavioral biological trial began by means of the Morris water maze (95-100 d). The trial comprised one test/learn unit of daily learning early and late for four days. The early unit begins with a run without a platform for 30 seconds, and the time in which the mouse stays in the quadrant in which the platform is usually located (target quadrant) is recorded. The other four runs are carried out with a hidden platform and with 4 variable starting positions.

Figure 2A:
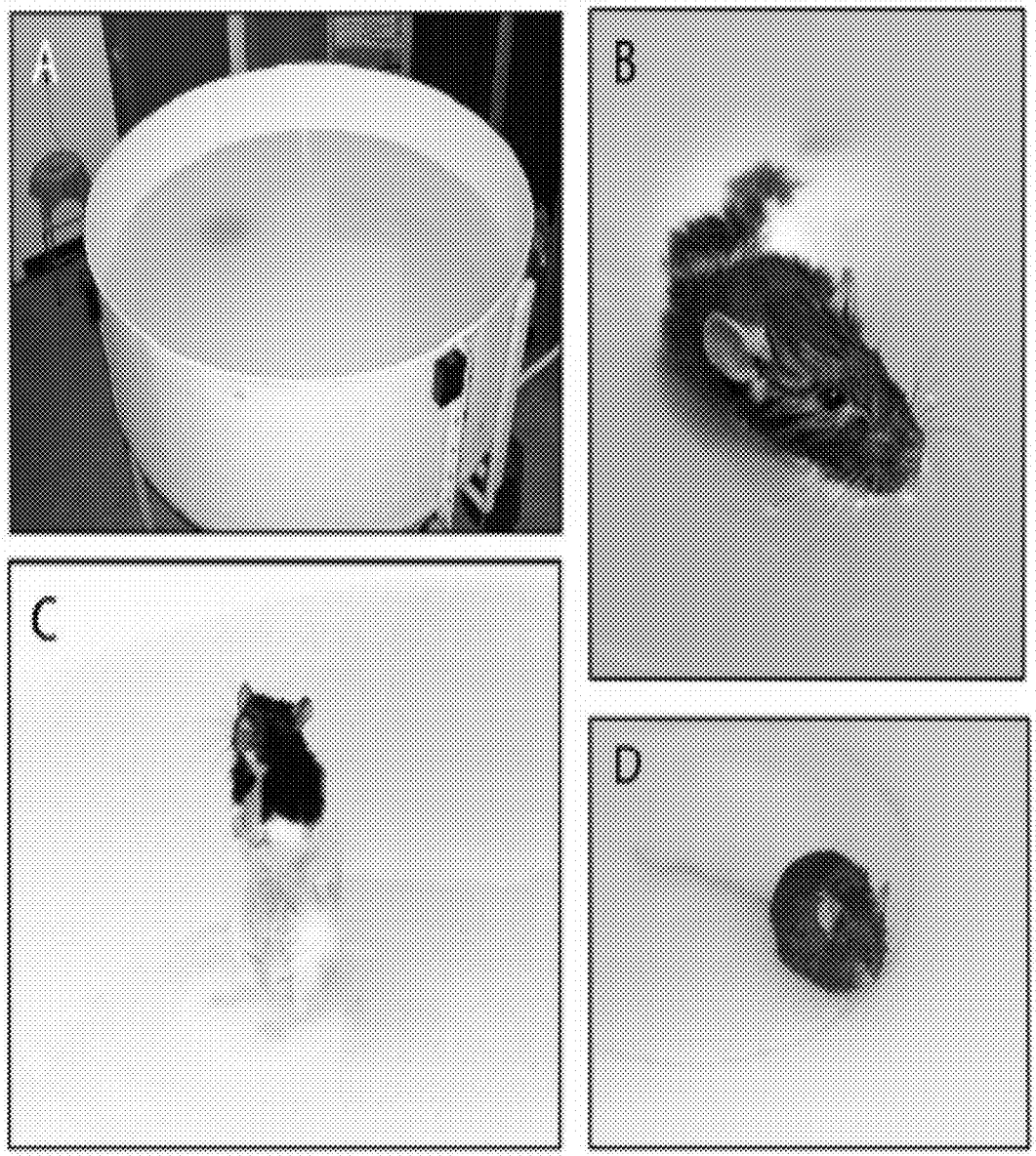
FIG. 2a shows a Morris water maze behavior test in vivo.
Figure 2B:
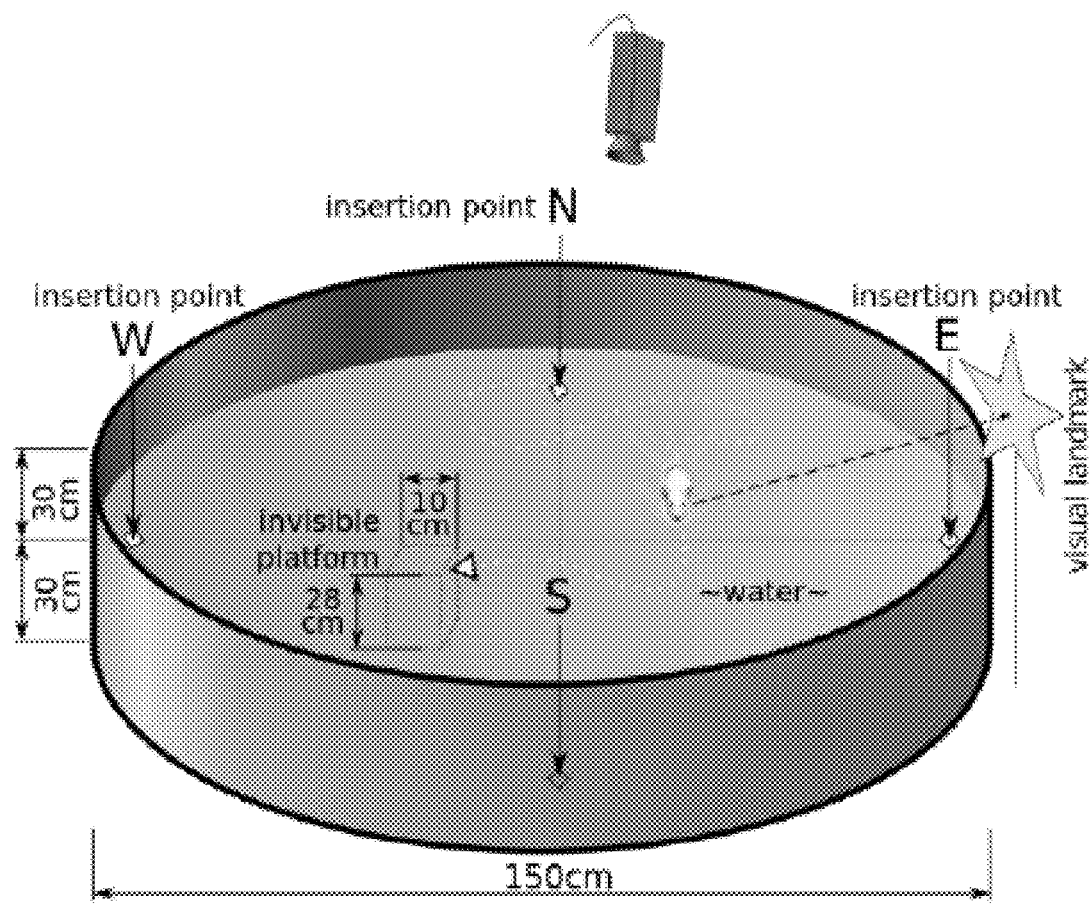
FIG. 2b shows the test set-up of the Morris water maze behavior test.
Figure 2C:
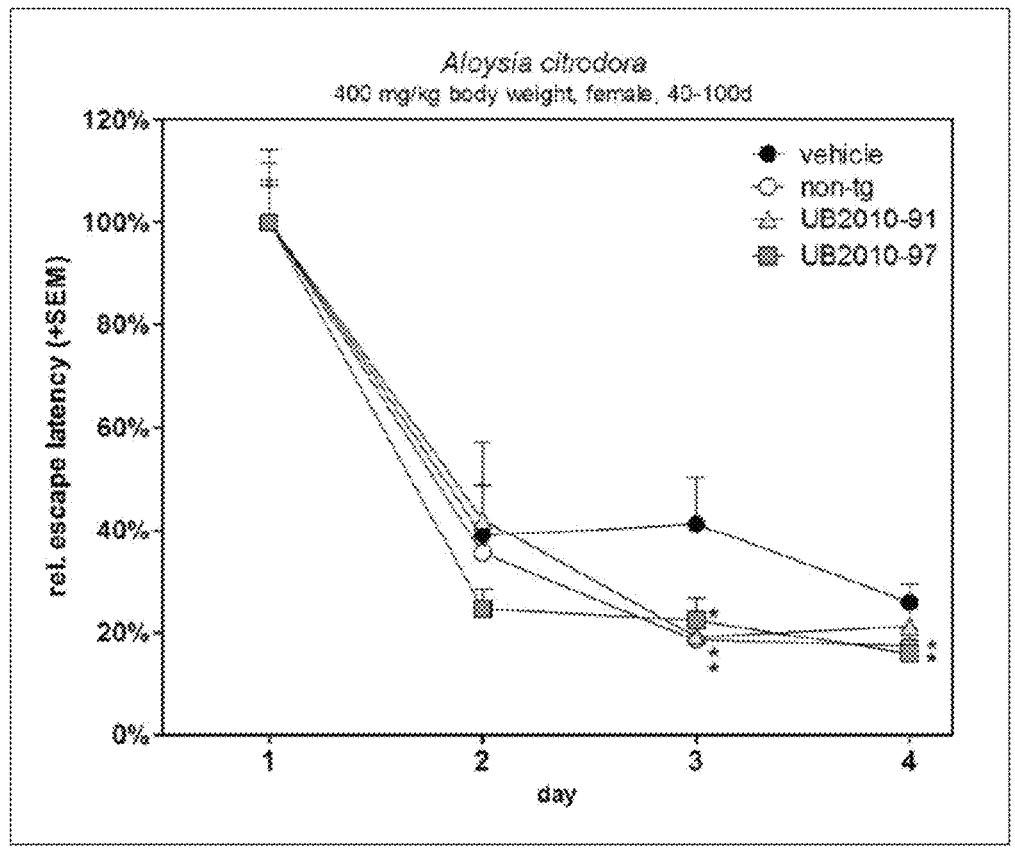
FIG. 2c shows the effect of lemon verbena extracts (20% v/v and 50% v/v EtOH) on the memory performance in a cognitive test model in mice (n=6).

The parameter analyzed was the time until reaching the platform (escape latency), graphically evaluated in FIG. 2. The evaluation shows that treatment with the lemon verbena extract according to the invention from 20% v/v EtOH leads to an impressive increase of the memory performance. Thus, the escape latency improved from relative 100% on day 1 to only 24.6% on day 2, or 22.4% on day 3. The slightly more lipophilic lemon verbena extract with 50% v/v EtOH augmented with some delay and reached the same order of magnitude. The escape latency improved from relative 100% on day 1 to 42.0% on day 2, and only 19.1% on day 3. Thus, the animals treated with lemon verbena extracts tended to be quicker already on days 2 and 3, and were significantly more quick on day 4 (p<0.05) in reaching the platform. On day 4, the learning performances of treated and healthy animals reach the same level in this model; however, they are significant different as compared to the transgenic animals with β-amyloid plaques. These results surprisingly show that lemon verbena extract is capable of increasing the cognitive performance Example 13: EEG Profiles on Healthy Rats Electroencephalography (from Greek encephalon=brain, graphein=write), abbreviated EEG, is a procedure of medical diagnosis for the measurement of the total electrical activity of the brain by recording voltage variations. The electroencephalogram offers a standardized study procedure in neurology as a graphic representation of such variations. For the clinical evaluation, a registration is required in at least twelve channels of different combinations of electrodes. The resulting data can be studied by expert specialists to determine striking patterns. A wide-spread mathematical method for analyzing the EEG is Fourier transformation into the frequency domain. Frequently the EEG is divided into frequency bands (so-called EEG bands), wherein the number of bands and the exact division is stated differently in part. The division of the frequency bands and their limits is historically conditioned and do not consistently coincide with boundaries that are considered useful due to more modern studies. Thus, for example, the theta band was divided into theta 1 and theta 2 intervals to consider the different meanings of the partial intervals. In particular, for long duration and sleep EEGs, software algorithms are used for assisted or automatic evaluation that reproduce a pattern recognition.

However, brain waves can not only be measured, but they can also be influenced. This can be done, inter alia, as neurofeedback, a special form of biofeedback, as a consequence of pharmacologically active substances, such as psychotropic drugs [Dimpfel W et al. (1996) Source Density Analysis of Functional Topographical EEG: Monitoring of Cognitive Drug Action. Eur J Med Res 1: 283-290]. The evaluation is also referred to as an electropharmacogram. In neurofeedback, it is usual to subdivide the EEG bands more finely and interpret them in more detail than in the classical EEG. An increased amplitude within the frequency ranges correlates with certain mental states or activities. Theta-2 waves can correlate, for example, with memory and learning ability, concentration, and/or creativity. Likewise, after extensive calibration, conclusions can be drawn to neurotransmitter-mediated SNC activities, which can be classified into dopaminergic, serotoninergic, cholinergic or noradrenergic subgroups.

A group of n=7 Fischer-344 rats were implanted in each case 4 semimicroelectrodes into the 4 brain areas "frontal cortex", "hippocampus", "striatum", and "formatio *reticularis*". The measurable changes of the potential field were transmitted by radio and evaluated to give an electropharmacogram.

The animals were treated with a lemon verbena dry extract formulation according to Example 3 with a dosage equivalent of 150 mg/kg of body weight. For this purpose, the individual doses were dissolved in water and administered once. Water served as a control experiment. After a pre-drug observing phase of 45 minutes, the test liquid was administered to the animals orally by gavage, followed by a setting phase of 5 minutes for the animal. Subsequently, the measurement was started for a measurement period of 5 hours. The frequency data were obtained by fast Fourier transformation (FFT) and averaged over periods of 60 minutes. The statistical evaluation was carried out by means of the Wilcoxon-Mann-Whitney U test against the control (water).

Figure 3A:
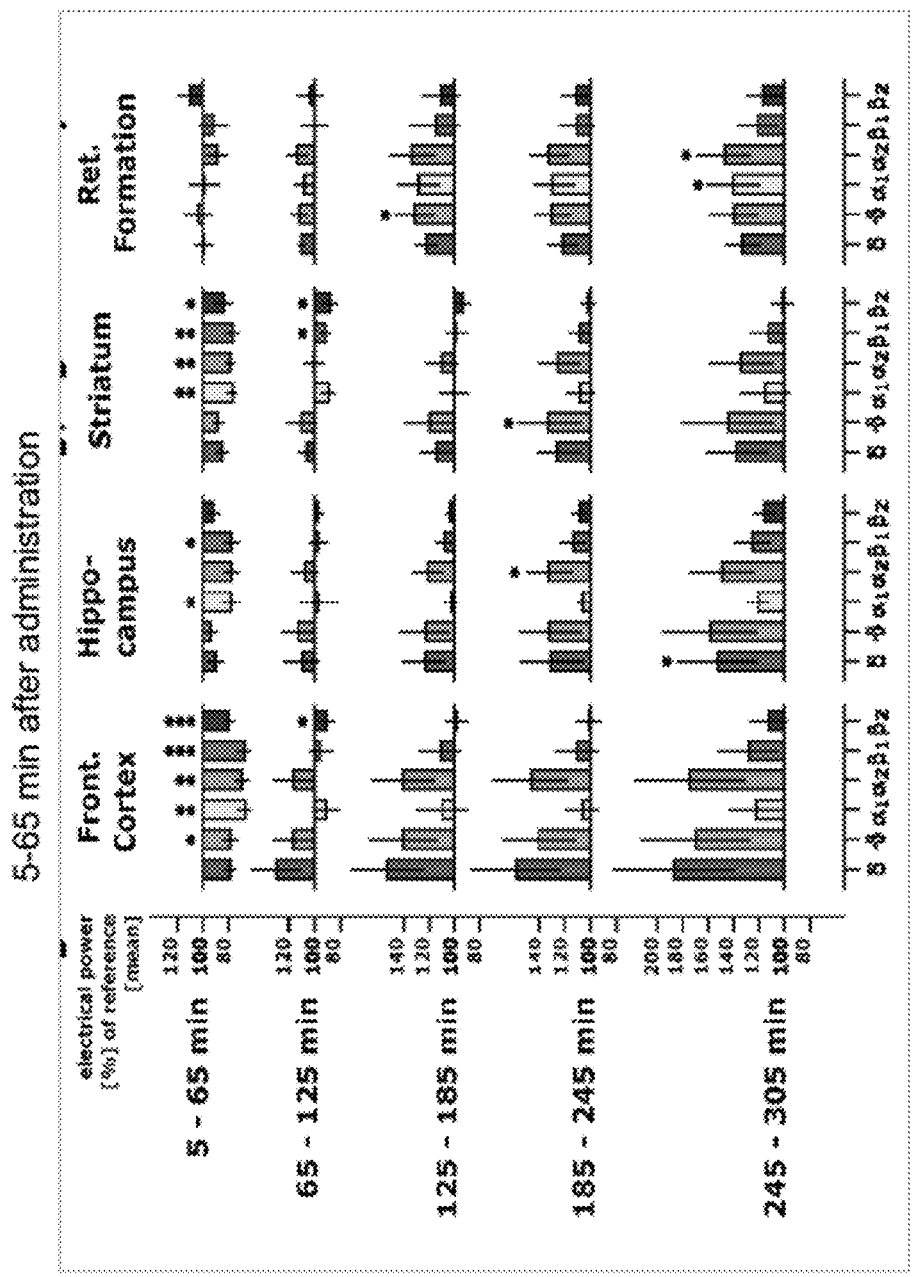
FIG. 3a shows a tele-stereo in vivo EEG determination; n=7 rats when using the lemon verbena extract according to the invention (50% v/v EtOH); 150 mg/kg of body weight, and a fast CNS activity within 65 min
Figure 3B:
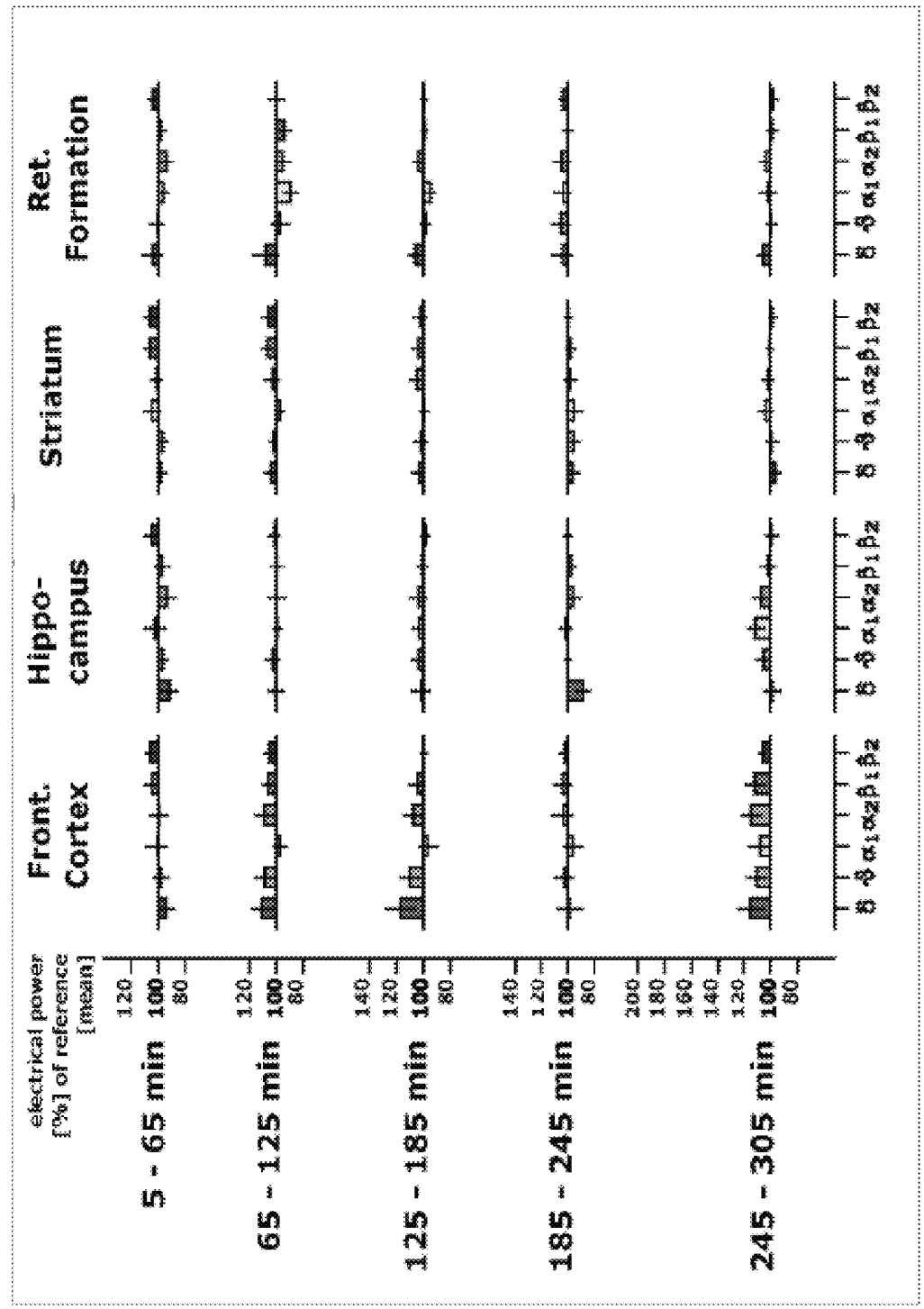
FIG. 3b shows a tele-stereo in vivo EEG determination in a control group in rats with the administration of water at 1 ml/kg of body weight.
Figure 3C:
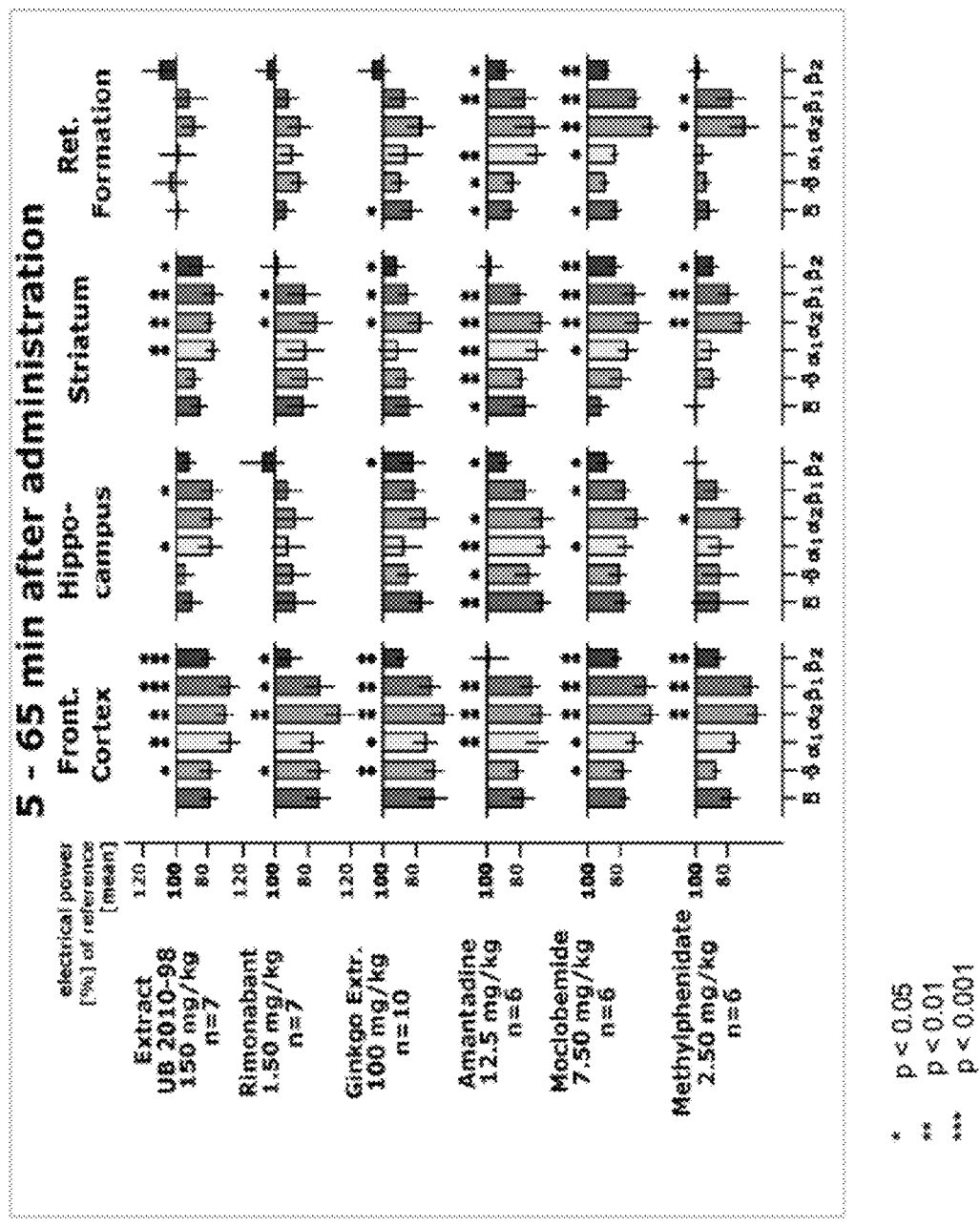
FIG. 3c shows a tele-stereo in vivo EEG determination when using the lemon verbena extract according to the invention (50% v/v EtOH)—batch UB2010-98 on healthy rats (n=8) as compared to synthetic active substances and ginkgo extract of Ph. Eur. grade.

The examination of a lemon verbena 50% v/v EtOH extract according to Example 3 showed a statistically significant change in different frequency bands within one hour after the administration (see FIG. 3, EEG graph). In particular, theta, alpha1, alpha2 and beta1 frequencies were affected, which indicates an influence on the noradrenergic, serotonergic, dopaminergic and glutaminergic systems. This complex kind of activity was previously observed in medicaments having an inhibiting effect on monoaminoxidase. Comparable electropharmacograms are seen for, for example, moclobemide, a monoaminoxidase inhibitor approved as an antidepressive, but also methylphenidate, a dopamine and noradrenaline reuptake inhibitor with additional agonistic activity on the serotonergic receptors 5-HT1A and 5-HT2B, approved for the treatment of ADHD.

These results show that the lemon verbena extract is suitable for treating ADHD.

In the serum of the mice, an increased level of the stress hormone cortisol was not found, which is why it can be considered that the usual mental stress of the measurement could be prophylactically prevented or at least decreased by the extract.

Also, an EEG profile comparable with that of a ginkgo extract (Ph. Eur. grade) could be seen, which shows the properties of lemon verbena extract for improving the cognitive performance. The data found in a rat EEG confirm the in vitro results obtained for neurotransmitter binding studies. To conclude, all preclinical data together give a clear evidence of the use of lemon verbena leaf extracts as CNS-active extracts, preferably in the application fields of improving the cognitive performance, or the attention deficit hyperactivity disorder.

The invention claimed is:

1. A method of treating a neurological disorder, the method comprising:
    providing a formulation to a person to treat a neurological disorder,
    wherein the neurological disorder is attention deficit hyperactivity disorder (ADHD), wherein the formulation comprises an extract prepared by alcoholic-aqueous extraction from leaves of lemon verbena (*Aloysia citriodora*) using an extractant having an alcohol concentration of 10-60% v/v and removal of volatiles by evaporation, wherein said extract has a content of essential oil of less than 0.05% by weight, based on the extract without additives.

2. The method according to claim 1, wherein said extract is obtained by extracting lemon verbena with mixtures of water and ethanol.

3. The method according to claim 1, wherein said extract is subjected to a secondary purification by removing lipophilic components by a liquid/liquid treatment with suitable solvents not miscible with water; or a liquid/solid treatment with suitable adsorber resins/adsorbents.

4. The method according to claim 1, wherein the formulation comprises fractions of the extract in a liquid or dried form.

5. The method according to claim 1, wherein the formulation further comprises chemical-synthetic substances and/or other plants in the form of plant parts and/or extracts.

6. The method according to claim 1, wherein said formulation is taken in orally.

7. The method according to claim 1, wherein said extract has a content of verbascoside of at least 2% by weight, based on the extract without additives.

8. The method according to claim 1, wherein said extract has a content of flavonoids of at least 0.05% by weight, based on the extract without additives.

9. The method according to claim 1, wherein said extract has a content of essential oil of less than 0.01% by weight, based on the extract without additives.

10. The method according to claim 2, wherein the ethanol has a concentration of 20-50% v/v.

11. The method according to claim 6, wherein said formulation comprises a medicament or a food supplement, and wherein the formulation comprises a beverage formulation, a tablet, a capsule, a lozenge, a chewing formulation, a wafer, or a fused tablet.

12. The method according to claim 1, wherein said extract has a content of verbascoside of at least 5% by weight, based on the extract without additives.

13. The method according to claim 1 further comprising identifying the neurological disorder prior to providing the formulation.

14. The method according to claim 1 wherein the extract is prepared without a secondary purification comprising removing lipophilic components by a liquid/liquid treatment with suitable solvents not miscible with water; or a liquid/solid treatment with suitable adsorber resins/adsorbents.

15. The method according to claim 1 wherein the neurological disorder is diagnosed using electroencephalography (EEG).

16. The method according to claim 15 wherein EEG is used to evaluate neurotransmitter-mediated central nervous system (CNS) activities related to dopaminergic, serotoninergic, cholinergic or noradrenergic subgroups.

* * * * *